United States Patent [19]

Rios et al.

[11] Patent Number: 4,983,846
[45] Date of Patent: Jan. 8, 1991

[54] PORTABLE FINGERPRINT DETECTION METHOD AND DEVICE

[75] Inventors: Arturo M. Rios, St. Petersburg; Michael Palermiti, Palm Bay, both of Fla.

[73] Assignee: Arturo M. Rios, Arecibo, P.R.

[21] Appl. No.: 397,132

[22] Filed: Aug. 22, 1989

[51] Int. Cl.$^5$ ............................. G01J 1/58; G01J 1/00
[52] U.S. Cl. ........................... 250/458.1; 250/459.1; 250/341; 250/504 H
[58] Field of Search ............... 250/458.1, 459.1, 461.1, 250/461.2, 341, 213 VT, 504 H

[56] References Cited

U.S. PATENT DOCUMENTS

| | | | |
|---|---|---|---|
| 3,811,777 | 5/1974 | Chance | 356/73 |
| 4,773,097 | 9/1988 | Suzaki et al. | 382/6 |
| 4,794,260 | 12/1988 | Asano et al. | 250/458.1 |

Primary Examiner—Constantine Hannaher
Assistant Examiner—Edward J. Glick
Attorney, Agent, or Firm—Rogers & Killeen

[57] ABSTRACT

A device and method for detecting fluorescent evidence, including fingerprints. The device and method use a pair of matched filters, a source of noncoherent light, and a light intensifier to detect the wavelength-shifted reflections from fluorescent substances. The light source and a first filter illuminate the substances with a light of predetermined band width. The second filter and the light intensifier detect and increase the luminance of the reflected light, shifted to a longer wavelength by reflection from the florescent substances. The device may be hand-held and portable.

27 Claims, 3 Drawing Sheets

PORTABLE FINGERPRINT DETECTION METHOD AND DEVICE

BACKGROUND OF THE INVENTION

The present invention relates to devices and methods for detecting evidence at, for example, the scene of a crime. More particularly, it relates to devices and methods for detecting fluorescent substances and other materials or features which may be made fluorescent, such as fingerprints.

The detection of objects or features not normally visible to the human eye has long been recognized as a significant problem, especially in the field of law enforcement where detection of evidence is of critical importance. In this field the effort has focused on the improvement of the detection of fingerprints.

Devices and methods for detecting fingerprints frequently use lasers because of the laser's high detection rate. The laser excites fluorescent substances carried by the fingerprint making the fingerprint visible. The laser may excite fluorescent substances in the fingerprint residue itself, or fluorescent substances deposited on and carried by the fingerprint such as powders, dyes or chemical reagents. Such devices may also be used to detect fluorescent evidence other than fingerprints such as certain fibers and sweat. See, for example, U.S. Pat. Nos. 4,708,882 and 4,794,260 to Asano, et al.

Lasers, however, present new problems to the crime scene investigator. Their portability is extremely limited and they may be unwieldy in confined spaces because they require a large power supply which must be transported to the scene. They may also be unsafe to operate because the laser beam itself is hazardous and caution must be taken so that it does not reach the human eye either directly or by reflection.

Fingerprints may, of course, be detected without lasers by using dusting powders, fuming and chemical reagents. Viewing may be enhanced by the use of ultraviolet light. See, for example, U.S. Pat. No. 4,504,408 to Morton. These techniques, however, generally have lower success rates than laser detection techniques. Old prints and prints on porous materials are particularly difficult to detect.

It is accordingly an object of the present invention to provide a novel device and method for detecting evidence, including fingerprints, that obviates the problems of the prior art and is portable and safe to use.

It is another object of the present invention to provide a novel device for detecting evidence, including fingerprints, without a laser, but with a relatively high degree of success.

It is yet another object of the present invention to provide a novel device for detecting evidence that illuminates fluorescent evidence with noncoherent light and detects the wavelength-shifted reflection from the evidence with a light intensifier.

It is still another object of the present invention to provide a novel device for detecting fluorescent evidence without lasers that uses light filters having non-overlapping bandwidths for forming an image of the fluorescent evidence.

It is a further object of the present invention to provide a novel method for detecting fluorescent evidence without laser that includes illuminating the evidence with a specifically filtered light and detecting and intensifying the wavelength-shifted reflection from the evidence.

It is yet a further object of the present invention to provide a novel method for detecting fingerprints using reflections of noncoherent light filtered so that only the images of the fingerprints are received and intensified.

It is still a further object of the present invention to provide an apparatus which can be used by police and similar departments for plural purposes in the investigation of crime scenes and criminal activity.

These and many other objects and advantages will be readily apparent to one skilled in the art to which the invention pertains from a perusal of the claims, the appended drawings, and the following detailed description of preferred embodiments.

THE DRAWINGS

DETAILED DESCRIPTION OF PREFERRED EMBODIMENTS

Figure 1:
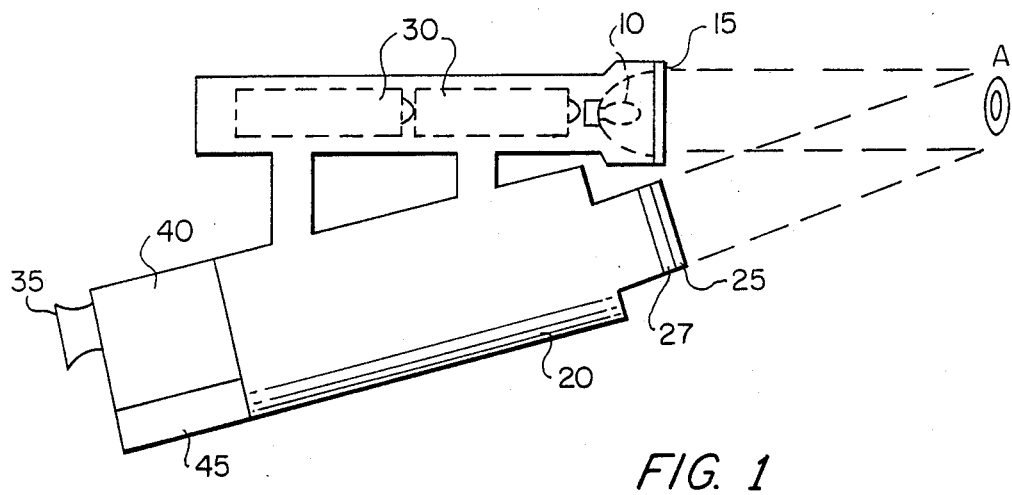
FIG. 1 is a pictorial representation of a side view of an embodiment of the detection device of the present invention.

With reference new to the figures where like elements have been given like numerical designations to enhance an understanding of the present invention, and particularly with reference to FIG. 1, the detection device of the present invention may include a source of noncoherent light 10 (lasers provide coherent light) for illuminating the evidence A, a first filter 15 for filtering light from the light source 10, a light intensifier 20 for receiving and intensifying light reflected from the evidence A, and a second filter 25 for filtering the reflected light before it is intensified.

In operation, the method and device of the present invention exploits the wavelength shift of light reflected from a fluorescent substance. As is well known, the wavelength of light is increased by about 10% upon reflection from a fluorescent substance (the light undergoes a Stokes shift). Thus, if a fluorescent substance is illuminated with light of a particular wavelength, the reflection may be detected at a longer wavelength.

In the present invention, light from light source 10 is filtered by filter 15 to illuminate a fluorescent substance with light having a predetermined band of wavelengths, for example, 555 to 565 nanometers. When a fluorescent substance is so illuminated, the reflections from the substance may be detected in a band of wavelengths about 10% longer; 610 to 622 nanometers in this example. By providing a second filter 25 that filters out light outside the wavelength band of the reflected light, only the desired reflections are detected. The filters 15 and 25 thereby cooperate to first illuminate and then enable detection of fluorescent substances.

To enhance detection of the reflections, a light intensifier 20 may be provided to increase the luminance of the reflections. The reflections have been found to be particularly dim, even when the source is bright. The intensifier increases the luminance of the reflections so that relatively high detection rates may be achieved.

To further enhance detection, the present invention may be operated when the fluorescent substances are shielded from all other light sources. By so doing, the intensifier does not receive light at the wavelength band of the second filter that may be reflected from objects other than those activated by the filtered light source.

The method of the present invention may also include the application of a fluorescent substance to evidence (e.g., fingerprint) s that its image may be more clearly seen. While any known application system is acceptable, dusting is preferred to enhance the portability of the present method and to reduce damage to the material bearing the fingerprints.

When a fine fluorescent dust is applied to a surface bearing a fresh fingerprint, the dust adheres more readily to the oil which forms the print than to the surrounding surface. The oil typically has been left in a pattern resembling the valleys between fingerprint ridges. Thus, the dust concentrates in a pattern resembling the fingerprint and the fingerprint fluoresces. If the fingerprint is not fresh or is dry, there is little or no oil on which the dust can adhere. However, in drying the oil typically turns into an amino acid which etches the surface at the submicron level. While such etching is often invisible to the naked eye, even if aided by conventional black fingerprint dusting powders, the fine dust of the fluorescing powder will be relatively more trapped by the etching traces and thereby reveal the ridge pattern of the of the fingerprint which originally was left on the surface.

With further reference now to FIG. 1, the light source 10 may be any source of noncoherent light, such as an incandescent lamp containing halogen or krypton with a tungsten filament. It is desirable that the source have a luminous intensity of about 100 lux. While a practical minimum intensity depends on the strength of the intensifier, it has been found that below about 25 lux the efficiency of the intensifier is reduced by the introduction of noise.

Light emitting diodes (LED) may be grouped and optically coupled to form a light source with a particular wavelength. LEDs, however, reduce the viewing area and have lower luminous intensity.

The first filter 15 may be any known fine-cut filter that is capable of creating a wavelength band (the one-half bandpass) of between 5 and 15 nanometers, with about 10 nanometers preferred. The center wavelength is desirably in the range of 500 to 600 nanometers, with about 560±4.8 nanometers preferred. In the 500–600 nanometer band, the preferred wavelength has been found to produce the highest overall detection rate of fluorescing evidence (e.g., fingerprints, body fluids, hair) on a wide variety of surfaces, such as paper, plastic, metal, wood and glass. The term "filter" as used herein also includes the elements in an LED that create a light source of a particular wavelength.

The second filter 25 may be identical to the first filter 15, except that the wavelength band should be correspondingly 10% higher.

The wavelength bands of filters 15 and 25 should not be so large that they overlap. If the bands were to overlap, reflected light that has not been wavelength shifted by the fluorescent material may be received, degrading operation of the device. A minimum separation of about 20 nanometers is desirable.

A lens 27 may be provided with the filter 25 to enhance the light-gathering power of the device. While a particular minimum power is not required, a power of f/2.0 or better (e.g., f/1.6) is preferred. Alternatively, or in addition, the filters may be in form of lenses.

The relatively broad wavelength band of the filters 15 and 25 (10 nanometers, as compared with 0.1 nanometers for lasers) increases the efficiency of the filters. For example, the first filter 15 may have an efficiency of 50% and the second filter 25, 90%. These relatively high efficiencies allow the use of a lower power intensifier 20. This is significant in the present invention because a low power intensifier has reduced energy requirements and increased portability.

The light intensifier 20 may be any known means for increasing the luminance of light it receives. While an intensifier capable of increasing luminance several thousand times is acceptable, an increase of about twenty thousand is preferred. Intensifier 20 may be, for example, a television system capable of detecting and intensifying low levels of light. A second generation microchannel plate is preferred because it provides low "blooming" (highly luminescent reflections do not wash out weaker reflections), high contrast and resolution, and is easily adapted for TV and photographic cameras.

The present invention may be completely portable. Batteries 30, such as common 1.5 volt dry cell batteries may be provided to power the light source 10 and intensifier 20. Appropriate circuitry may be provided so that the device may operate from household current as well.

The images produced by the intensifier may be viewed through an eyepiece 35 that may be focused. The images may be reproduced with a camera 40, such as a photographic or television camera. A remote monitor may also be provided. A video recording system 45 may be included so that images may be replayed later.

Figure 2:
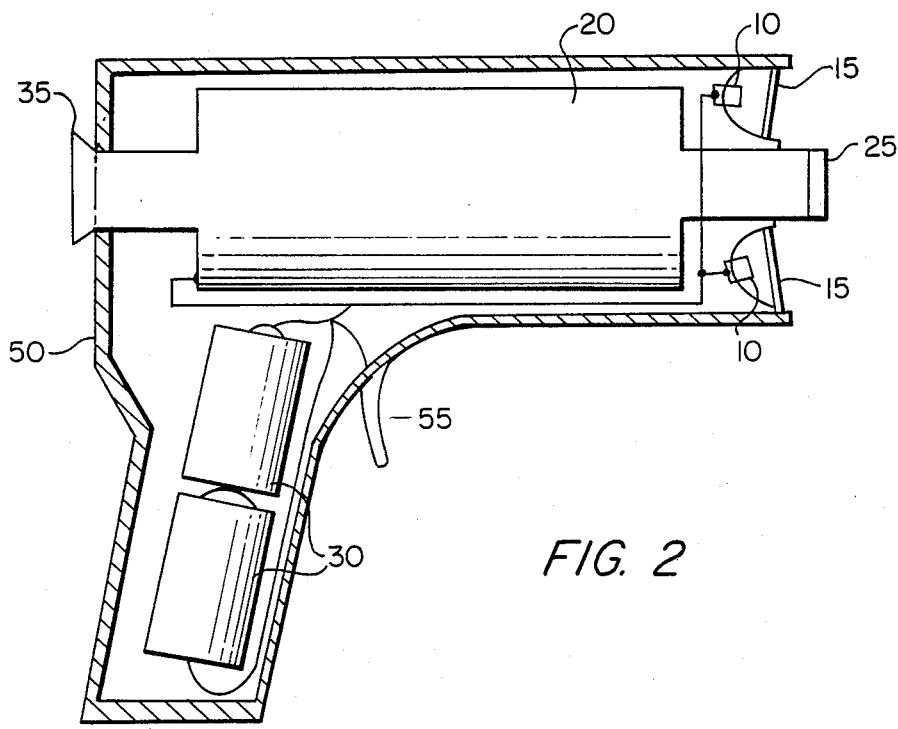
FIG. 2 is a pictorial representation of a sectional side view of another embodiment of the detection device of the present invention.
Figure 3:
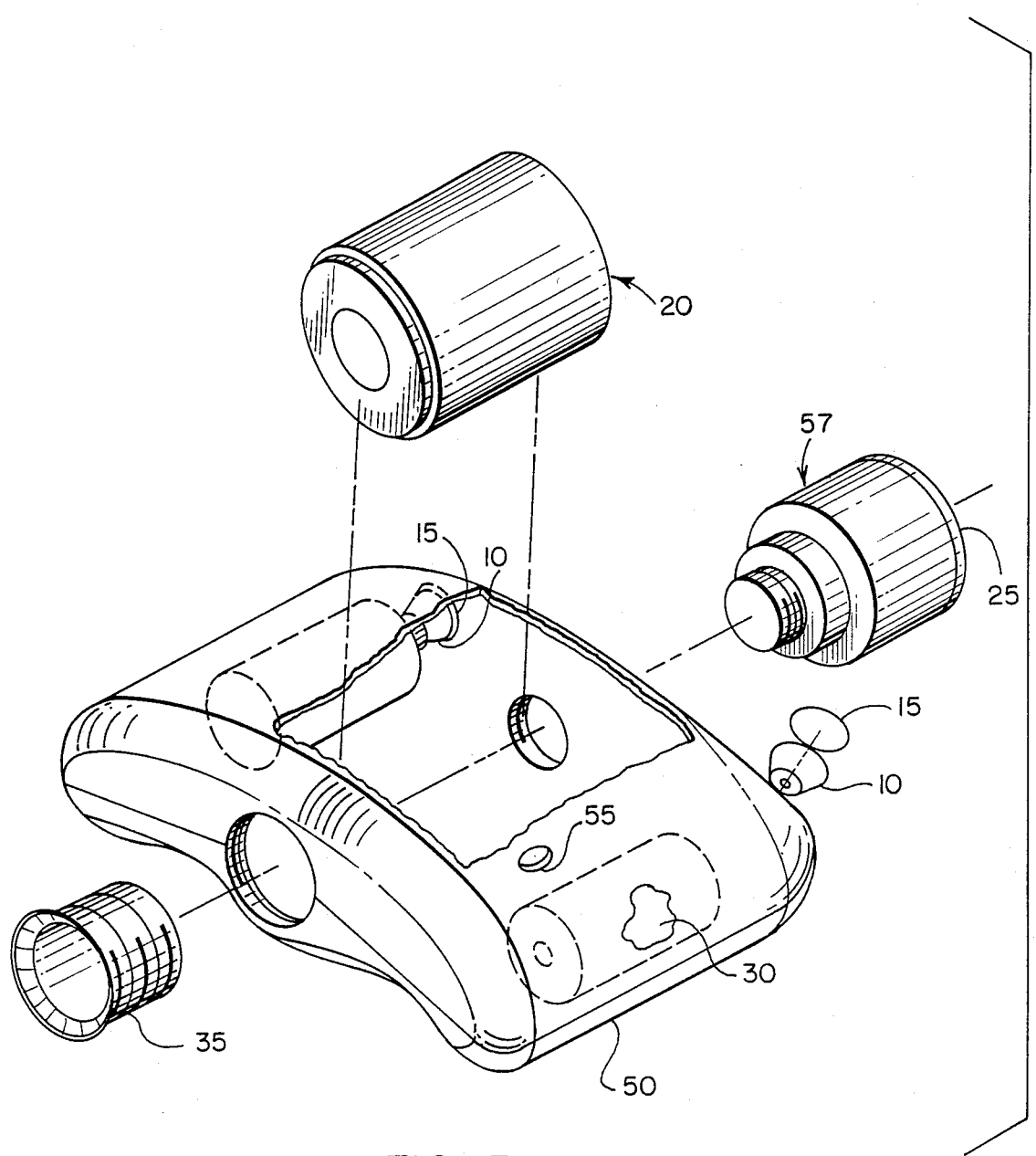
FIG. 3 is an exploded pictorial representation of a further embodiment of the present invention.

With reference now to FIGS. 2 and 3, other embodiments of the present invention may include two or more filtered light sources 10. The light sources 10, intensifier 20, filters 15 and 25, and batteries 30 may be carried in a impact-resistant case 50 configured with a trigger 55 to operate the device. As seen in FIG. 3, a 50 millimeter f/1.6 TV lens 57 may be provided to cooperate with a 25 millimeter micro-channel plate intensifier 20. The embodiment of FIG. 3 may provide a two inch diameter viewing area eight inches from the lens 57.

Figure 4:
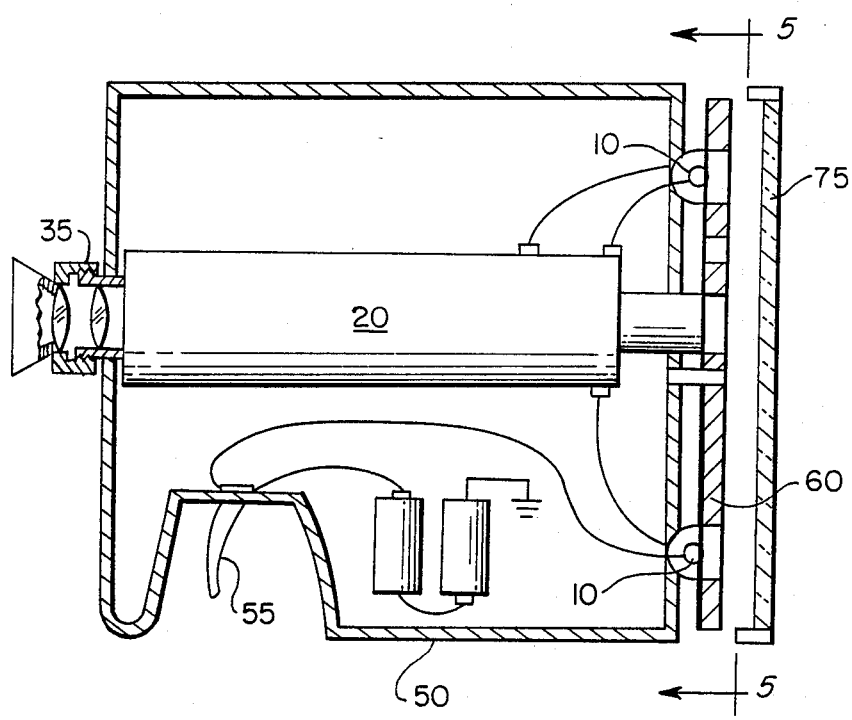
FIG. 4 is a pictorial representation of a side view of another embodiment of the present invention showing a multiple filter capability.
Figure 5:
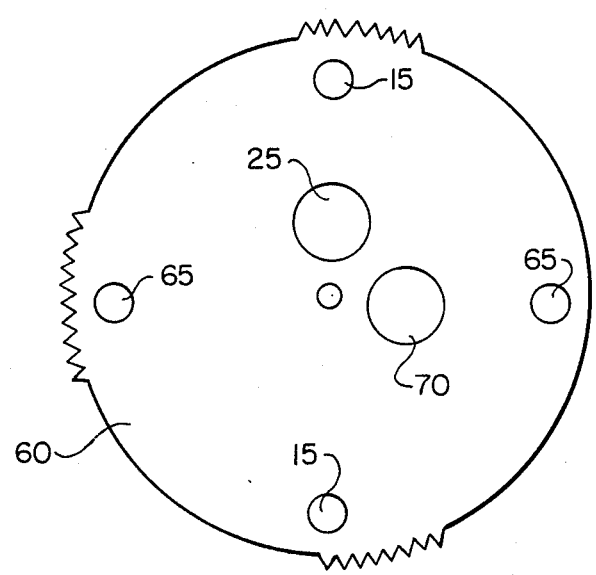
FIG. 5 is a pictorial representation of a front view of the multi-filter disk shown in FIG. 4.

In an additional embodiment, and with reference to FIGS. 4 and 5, the present invention may include selectable filters to provide additional capability. For example, the present invention may be used as a night scope by placing an infrared filter in front of the light source and removing the filters from the light intensifier. Other filter combinations may be obvious to those skilled in the art.

The present invention may include a knurled wheel 60 moveably affixed to case 50 which may be rotated to place various sets of filters in registration with the sources of light 10 and the intensifier 20. First filter 15 and second 25 may form one such set of filters, and infrared filter 65 and clear sheet 70 another. A plate of clear material 75 may be provided to protect the wheel assembly.

While preferred embodiments of the present invention have been described, it is understood that the embodiments described are illustrative only and that the scope of the invention is to be defined solely by the appended claims when accorded a full range of equivalence, many variations and modifications naturally occurring to those skilled in the art from the perusal thereof.

We claim:

1. A portable device for detecting fingerprints without a laser by illuminating a fingerprint which has been made fluorescent, and receiving the wavelength-shifted reflections from the fluorescent fingerprint, comprising:
   (a) a noncoherent light source for illuminating a fingerprint;
   (b) a first filter for filtering light from said light source, said first filter having a first predetermined center wavelength between 500 and 600 nanometers;
   (c) a light intensifier for receiving reflections from the illuminated fingerprint and for intensifying the reflections at least several thousand times;
   (d) a second filter for filtering light received at said light intensifier, said second filter having a second predetermined center wavelength,
   said second center wavelength being separated from said first center wavelength by approximately the wavelength shift caused by reflection from the fluorescent fingerprint, and
   said first and second filters each having a one-half bandpass much less than said wavelength shift; and
   (e) means for viewing the intensified reflections so that fingerprints may be detected.

2. The device as defined in claim 1 wherein said light source comprises an incandescent lamp.

3. The device as defined in claim 2 further comprising one or more batteries for powering said light source and said intensifier.

4. The device as defined in claim 3 wherein each said one half bandpass is between five and fifteen nanometers.

5. The device as defined in claim 4 wherein said first center wavelength is approximately 560 nanometers.

6. The device as defined in claim 5 wherein said second center wavelength is approximately 615 nanometers.

7. The device as defined in claim 6 wherein each said one-half bandpass is approximately ten nanometers.

8. The device as defined in claim 1 wherein said means for viewing the reflections comprises a television camera.

9. The device as defined in claim 8 further comprising means for recording the intensified reflections.

10. The device as defined in claim 1 wherein said means for viewing the reflections comprises a photographic camera.

11. The device as defined in claim 1 wherein said light intensifier intensifies the reflections approximately 20,000 times.

12. The device as defined in claim 1 wherein said second filter comprises a lens of at least f/2.0.

13. The device as defined in claim 1 further comprising means for selectably removing said first and second filters from registration with said light source and said intensifier, and providing as respective replacements therefore, third and fourth filters having center wavelengths and one-half bandpasses different from said first and second filters.

14. The device as defined in claim 13 wherein said third filter comprises an infrared filter and said fourth filter admits all light.

15. The device as defined in claim 13 wherein said means for removing comprises a rotatable wheel having pairs of openings for all said filters corresponding to said light source and said intensifier.

16. A portable device for detecting fingerprints that are fluorescent comprising:
   (a) a source of noncoherent light having a first wavelength band for illuminating an entire fingerprint;
   (b) a receiver for intensifying light of a second wavelength band reflected from the illuminated fingerprint, said second wavelength band not overlapping said first wavelength band; and
   (c) means for forming an image of an entire fingerprint from the intensified light.

17. A device for selectably detecting evidence and infrared light comprising:
   (a) a noncoherent light source;
   (b) a light intensifier for intensifying light received therein at least several thousand times;
   (c) a first set of filters comprising,
      a first filter having a first center wavelength for filtering light from said light source, and
      a second filter having a second center wavelength for filtering light received at said light intensifier,
      said first and second center wavelengths being separated by the wavelength shift caused by reflection of light from a fluorescent substance, and
      the one-half bandpass of each of said first and second filters being much less than said wavelength shift;
   (d) a second set of filters comprising,
      an infrared filter for filtering light from said light source, and
      a clear glass for admitting all light received at said light intensifier;
   (e) means for selectably positioning either said first set of filters or said second set of filters in registration with said light source and said intensifier; and
   (f) means for viewing the image intensified by said intensifier.

18. The device as defined in claim 17 wherein in said means for positioning comprises a rotatable wheel carrying said first and second sets of filters.

19. A method for detecting fingerprints without a laser, comprising the steps of:
   (a) illuminating a fingerprint with a noncoherent light source;
   (b) filtering light from said light source with a first filter so that light reaching the fingerprint has a first predetermined center wavelength between 500 and 600 nanometers;
   (c) intensifying light reflected from the fingerprint at least several thousand times;
   (d) filtering light reflected from the fingerprint with a second filter so that the intensified light has a second predetermined center wavelength longer than said first wavelength,
      the difference between said first and second wavelengths being approximately equal to the wavelength shift caused by reflection from the fluorescent fingerprint, and
      the one-half bandpasses of said first filter and said second filter being much less than said wavelength shift; and
   (e) creating an image of the intensified light so that fingerprints may be detected.

20. The method as defined in claim 19 wherein said noncoherent light source comprises an incandescent lamp.

21. The method as defined in claim 20 wherein said one-half bandpass is between five and fifteen nanometers.

22. The method as defined in claim 21 wherein the reflected light is intensified approximately 20,000 times.

23. A method for detecting fingerprints comprising the steps of:
    (a) providing a fluorescent substance to be carried by fingerprints;
    (b) illuminating the fingerprints carrying said fluorescent substance with noncoherent light having a first wavelength band; and
    (c) intensifying light having a second wavelength band reflected from the illuminated fingerprints,
        the difference between the centers of said first and second wavelength bands being approximately equal to the wavelength shift caused by reflection from the fluorescent substance, and
        said first and second wavelength bands are not overlapping.

24. A method for detecting fluorescent fingerprints comprising the steps of:
    (a) receiving reflections from a fluorescent fingerprint illuminated with noncoherent light having a relatively narrow wavelength band;
    (b) filtering the received reflections so that only images of the fluorescent fingerprint are presented; and
    (c) intensifying the images presented so that the fingerprint may be detected.

25. A device for detecting evidence, including fingerprints, without a laser by illuminating evidence which is fluorescent, and receiving the wavelength-shifted reflections from the fluorescent evidence, comprising:
    (a) a noncoherent light source for illuminating evidence;
    (b) a first filter for filtering light from said light source, said first filter having a first predetermined center wavelength;
    (c) a light intensifier for receiving reflections from the illuminated evidence and for intensifying the reflections at least several thousand times;
    (d) a second filter for filtering light received at said light intensifier, said second filter having a second predetermined center wavelength,
        said second center wavelength being separated from said first center wavelength by approximately the wavelength shift caused by reflection from the fluorescent evidence, and
        said first and second filters each having a one-half bandpass much less than said wavelength shift;
    (e) means for selectably removing said first and second filters from registration with said light source and said intensifier, and providing as respective replacements therefore, third and fourth filters, wherein
        said third filter comprises an infrared filter and said fourth filter admits all light; and
    (f) means for viewing the intensified reflections so that evidence may be detected.

26. The device as defined in claim 25 wherein said means for removing comprises a rotatable wheel having pairs of openings for all said filters corresponding to said light source and said intensifier.

27. A portable device for detecting fingerprints that have been made fluorescent comprising:
    (a) a noncoherent light source for illuminating an area approximately at least the size of an entire fingerprint;
    (b) a first filter for filtering light from said light source, said first filter having a first predetermined center wavelength;
    (c) a light intensifier for receiving reflections from the illuminated area and for intensifying the refections at least several thousand times;
    (d) a second filter for filtering light received at said light intensifier, said second filter having a second predetermined center wavelength,
        said second center wavelength being separated from said first center wavelength by approximately the wavelength shift caused by reflection from a fluorescent fingerprint in the area, and
        said first and second filters each having a one-half bandpass much less than said wavelength shift;
    (e) means for viewing the intensified reflections from an entire fingerprint so that fingerprints may be detected; and
    (f) means for powering said device with a battery carried by a user,
        said device being adapted to be hand held and carried to an area containing fingerprints by a user.

* * * * *